US009702857B2

(12) United States Patent
Davis et al.

(10) Patent No.: US 9,702,857 B2
(45) Date of Patent: Jul. 11, 2017

(54) ANALYSIS REAGENTS AND METHOD

(75) Inventors: Stephen Charles Davis, Ascot (AU); John David Petty, Holland Park West (AU)

(73) Assignee: AQUALYSIS PTY LTD, Ascot, Queensland (AU)

( * ) Notice: Subject to any disclaimer, the term of this patent is extended or adjusted under 35 U.S.C. 154(b) by 651 days.

(21) Appl. No.: 13/696,121

(22) PCT Filed: May 4, 2011

(86) PCT No.: PCT/AU2011/000511
§ 371 (c)(1),
(2), (4) Date: Nov. 5, 2012

(87) PCT Pub. No.: WO2011/137484
PCT Pub. Date: Nov. 10, 2011

(65) Prior Publication Data
US 2013/0052742 A1    Feb. 28, 2013

(30) Foreign Application Priority Data
May 5, 2010    (AU) ................................ 2010901916

(51) Int. Cl.
*G01N 21/80*    (2006.01)
*G01N 31/22*    (2006.01)
(Continued)

(52) U.S. Cl.
CPC ............. *G01N 31/22* (2013.01); *G01N 21/80* (2013.01); *G01N 21/78* (2013.01); *G01N 33/1853* (2013.01)

(58) Field of Classification Search
CPC .... G01R 33/60; G01N 33/0037; G01N 33/84; G01N 33/721; G01N 33/4925; A61B 5/150755
(Continued)

(56) References Cited

U.S. PATENT DOCUMENTS 3,718,605 A    2/1973    Storm
4,092,115 A    5/1978    Rupe et al.
(Continued)

FOREIGN PATENT DOCUMENTS

WO    WO-2008061315 A1    5/2008
WO    WO-2009047731 A3    9/2009

OTHER PUBLICATIONS

Flury et al.(1994) Journal of Environmental Quality.23:5. Brilliant Blue FCF as a Dye Tracer for Solute Transport Studies a Toxilogical Overview.*
(Continued)

*Primary Examiner* — Rebecca M Fritchman
(74) *Attorney, Agent, or Firm* — Polsinelli PC (57) ABSTRACT

The invention provides a single colorimetric reagent for the measurement of oxidizing agents such as free chlorine in a liquid sample which contains a food dye, whereby the oxidizing agent undergoes a reaction with said food dye. A preferred food dye is Brilliant Blue FCF. There is also provided a control system for regulating the volume of reagent added to a fixed volume of sample according to a control algorithm to give a chosen excess of a reagent compound beyond that required to stoichiometrically react with the target analyte in the sample. Also disclosed are single reagents for colorimetric determination of total alkalinity and calcium hardness.

18 Claims, 4 Drawing Sheets

(51) Int. Cl.
*G01N 21/00* (2006.01)
*G01N 21/78* (2006.01)
*G01N 33/18* (2006.01)

(58) Field of Classification Search
USPC .............................................. 600/573; 436/79
See application file for complete search history.

(56) References Cited

U.S. PATENT DOCUMENTS

| | | | |
|---|---|---|---|
| 5,155,048 A * | 10/1992 | Williams | G01N 31/22 436/124 |
| 5,491,094 A | 2/1996 | Ramana et al. | |
| 7,441,472 B2 | 10/2008 | Vinton | |
| 7,491,546 B2 * | 2/2009 | Jaunakais | G01N 31/224 356/436 |
| 2003/0166295 A1* | 9/2003 | Fukuoka | C12Q 1/28 436/145 |

OTHER PUBLICATIONS

"VISOCOLOR® ECO free chlorine 2", retrieved from <URL: http://www.mn-net.com/tabid/10294/default.aspx> Mar. 12, 2010.
"Brilliant Blue FCF", retrieved from <URL: http://en.wikipedia.org/wiki/Brilliant_Blue_FCF> Feb. 7, 2009.
<URL: http://www.goehler-hplc.de/en/mnrapid.phtml?page=4> Mar. 12, 2010.

\* cited by examiner

ANALYSIS REAGENTS AND METHOD

PRIORITY

Priority is claimed as a national stage application, under 35 U.S.C. §371, to PCT/AU2011/000511, filed May 4, 2011, which claims priority to Australian Application No. 2010901916, filed May 5, 2010. The disclosures of the aforementioned priority applications are incorporated herein by reference in their entirety.

This invention relates to reagents for use in colorimetric measurement of an analyte in liquid samples, especially for water analysis, and a control method for regulating said reagents in performing the analysis. The invention is suited for commonly measured analytes in water such as but not limited to free chlorine (or other oxidising agents), total alkalinity, calcium hardeners and pH. While the reagents and method described hereto are especially suited for on-line analysis, they may be used with laboratory instruments, hand-held instruments and the like.

BACKGROUND TO THE INVENTION

Although a number of compounds have been experimented with to measure free chlorine, the measurement of free chlorine in water involving the formation or loss of coloured species
has long been determined by three principal methods:
(1) titrimetry where free chlorine stoichiometrically reacted with a reducing agent such as ferrous ion to an end-point utilising a redox indicator such as N,N-Diethyl-p-phenylenediamine (DPD).
(2) colorimetry where an excess of a colourless reagent reacts with free chlorine to produce a coloured reaction product proportional to the concentration of free chlorine. For example, DPD reacts with free chlorine to produce a pink colour.
(3) Bleaching of methyl orange.

Reactions involving production or loss of colour can be monitored accurately by measuring absorption at one or more wavelengths.

Method (1) has the disadvantage that a dilute solution of ferrous ion is readily oxidised by dissolved oxygen. This necessitates the use of fresh titrant. Moreover, at the commonly measured concentrations of free chlorine between 0-5 ppm, the end-point is not sharp.

DPD, the most popular reagent of Method (2) is injurious to health. The solid may be fatal if absorbed through the skin (ref: MSDS Oxford University). This risk is reduced for DPD in solution, but poses a concern where an on-line swimming pool or spa analyser utilises a reservoir of DPD. If the analyser malfunctions and a significant amount of DPD is discharged into the water, the health of a bather could be affected, especially in the case of a small body of water, as in a spa.

Methyl orange is also injurious to health. Bleaching methods can potentially measure a larger range of free chlorine concentrations, but enough of the compound being bleached must be added to ensure all of the free chlorine present reacts. It is also necessary to know the volume which has been added in order to calculate the concentration of free chlorine.

As on-line analysers using colorimetric methods consume part of the body of water they measure, this may result in a significant loss of water over time if the reagent/water mixture is expelled to waste. This is undesirable in areas where water conservation is paramount. Moreover, consideration must be given to the safe disposal of the spent reagent/sample mixtures.

Many of the methods of the prior art involve several separate reagents which are dispensed from separate reagent reservoirs. This requires complex and expensive measuring apparatus For example the Standard Method for the measurement of free chlorine involves separate solutions of DPD, and buffer.

European patent 762120 discloses a method of determining chlorine content by using a benzidine indicator which forms a dye by reaction with chlorine.

U.S. Pat. No. 4,092,115 discloses using an azine indicator for chlorine analysis.

U.S. Pat. No. 7,441,472 discloses a method and device for measuring chlorine content in swimming pools.

U.S. Pat. No. 7,491,546 discloses a touch free method of chlorine analysis.

WO2008061315 by the present applicant discloses apparatus and method for determining chlorine content is a swimming pool.

It is an object of the present invention to provide a reagent for the measurement of free chlorine which is not injurious to health, and may be safely discharged into water used for drinking or swimming purposes, thereby allowing for the recycling of spent reagent/sample mixtures of free chlorine back into the body of water being measured, in order to conserve water.

It is preferred object of the present invention to provide a control system in order to regulate the addition of a reagent to provide a simple, accurate and reliable addition of said reagent to a fixed volume of sample fluid to be measured.

It is another preferred object of the invention to provide a concentrated reagent to minimise reagent consumption and so that the addition of the reagent to the fixed volume of sample causes a negligible dilution of the sample. It is also an object of the invention to use single reagents within which all the required components have a stable coexistence to simplify the dispensing system, and to increase the speed of the method by using a single injected volume as opposed to a titrimetry process where multiple injections are required.

Yet another preferred object of the invention is to allow accurate measurements of free chlorine over a wide range of concentration without need for dilution of the sample, typically 0-25 ppm.

BRIEF DESCRIPTION OF THE INVENTION

This invention provides a colorimetric reagent containing a food dye for the measurement of oxidising agents such as free chlorine in a liquid sample, whereby the oxidising agent undergoes a reaction with said food dye.

Based on this development the present invention also provides an analytical method for utilising the abovementioned reagent. This method is also applicable to prior art wet chemistries for other analyses such as the well known measurement of pH by phenol red indicator, and titrometric analyses for total alkalinity and hardness.

In the case of free chlorine measurement the present invention is predicated on the realisation that certain FDA approved food dyes can be bleached by free chlorine, or are capable of acting as redox indicators, whereby the parent dye reacts with free chlorine to give a coloured product which has a significantly different absorption spectrum to the parent dye. For the reaction to occur rapidly the solution must be acidified. The use of a reagent based on substances approved for use in foods ensures that the reagent is completely safe, and may even be dispensed back into drinking water.

While several common food dyes such as cochineal can be bleached by free chlorine, Brilliant Blue FCF (Food Dye Code E133) acts as a redox indicator. The reaction with free chlorine produces a stable yellowish reaction product. Unlike the bleaching reaction where the product is colourless, a redox indicator has an advantage that, if the reaction product is coloured, it can be measured as well as, or alternatively to, the loss of the parent dye. The reaction between brilliant blue FCF and free chlorine is ideally performed in the pH range 1.5-2.5 where the reaction is instantaneous and complete. It has been found in practice the reaction with combined chlorine does takes place, but much more slowly, similar to the case with DPD. Unlike DPD, Brilliant Blue FCF solution is indefinitely stable in air The reaction is insensitive to calcium and other trace metals, and to total alkalinity provided the solution is acidified or buffered to below a maximum pH (for example 2.8).

Other examples of synthetic dyes approved for use in foods are Indigotine, Fast Green FCF, Allura Red AC, Erythrosine, Tartrazine and Sunset Yellow FCF. Other examples of natural food colourings are caramel colouring, annatto, betanin, turmeric, saffron, paprika and elderberry juice.

The invention further incorporates one of the abovementioned dyes, or other dye or coloured species which is bleached or acts as a redox indicator with oxidising agents such as free chlorine, into a measurement system whereby the amount of added reagent can be accurately quantified and regulated. This is of particular use in an on-line analyser which continually monitors the free chlorine level.

In the prior art DPD method, the reagent is effectively colourless and a coloured reaction product is produced. In this case the DPD needs to be added in excess to ensure a sufficient amount is available to react with any free chlorine. In the method of this invention the reagent is coloured and the reaction either removes the colour of the reagent or transforms some of the reagent into a different colour. In either case, as with the DPD reaction, the reagent must be added in excess to ensure all the free chlorine in the sample has reacted.

In the case where the reagent is bleached to a colourless product, the concentration of free chlorine is determined from a loss of colour. The presence of reagent colour indicates there is excess reagent present, and to calculate the loss of colour (and hence amount of free chlorine) the original amount of reagent added must be accurately known. A fixed amount of reagent can be added, but this would have to contain enough reagent to cover the free chlorine concentration range of interest. There are two main disadvantages to this approach. Firstly this will be wasteful of reagent, the most economical use of the reagent would be to use only a small excess to the amount needed to react with the free chlorine concentration present. Secondly at very low free chlorine concentrations most of the reagent will remain unreacted and there will be a limit to the amount of reagent colour which can be measured, and hence there will be a limited concentration range which can be measured by adding a fixed volume of reagent. If the volume added is known, it can be regulated so as to add only a small excess to what is needed, and larger concentration ranges can be measured.

In the case where the reagent is oxidised to a different coloured product, some reagent must remain after the reaction to ensure enough has been added, and the concentration of free chlorine can be calculated from the amount of coloured product. Again a fixed volume of reagent sufficient to cover the free chlorine range of interest can be added. In this case it is not necessary to have the volume added so precisely known, since the free chlorine is calculated from the product formed and it is only necessary to have excess reagent, as indicated by the presence of unreacted reagent. However again this is not the most economical use of reagent and it would be better to regulate the volume added. In practice it will also generally be the case that there will be some degree of overlap of the absorption spectrums of the reagent and coloured oxidation product and it will be necessary to derive the amount of excess reagent present to make the appropriate corrections in calculating the free chlorine concentrations.

In another aspect this invention involves providing single reagents with a control algorithm to regulate the volume of reagent added to a fixed volume of sample to give a chosen excess of reagent beyond that required to stoichiometrically react with the target analyte present in the water. However it will be appreciated that the reagents described can also be applied in manual tests kits or other off-line instrumentation, and that the described control algorithm can be applied to other on-line analysers using more than one reagent solution.

The control system of this invention for determining the free chlorine concentration when a dye is oxidised to a colourless or coloured product is based on knowing or deriving the volume of reagent added and the amount of reagent remaining in excess after reaction. The volume added may be known, for example from an accurate delivery mechanism (such as a syringe pump or other dispensing device) or may be derived, for example from optical measurements.

In a preferred method the steps include
Adding an amount of concentrated reagent containing a known concentration of the reactant compound to a water sample to be analysed in a first analysis cycle.
Mixing said reagent and water sample to form a solution
Measuring the absorbance of the solution at 2 or more wavelengths
Determining from said absorbance measurements the concentrations present in the solution of un-reacted reactant compound and reaction product
If there is un-reacted reactant present, determining the concentration of target analyte present in the solution from the reaction product concentration
Determining a "total" concentration of reactant in the solution (defined as the total concentration of reactant if there were no conversion to product) from the un-reacted concentration, the product concentration and stoichiometry of the reaction producing the reaction product from the reactant
Determining a new volume Vnew to be added to produce a chosen excess level of reactant above that required for reaction with the analyte concentration in the water sample
Regulating the dispensing system to dispense Vnew in a subsequent analysis cycle
An alternative method includes
Adding a coloured (reference) compound to the reagent which does not take part in the reaction and has an absorption spectrum significantly different to other compounds in the reagent and to products formed when added to the water sample, and wherein the reference compound is present in the reagent in a known concentration ratio to a reactant compound in the reagent, such that the concentration of the reactant compound may be expressed as some factor F multiplied by the concentration of the reference compound.

Adding reagent to the water sample being analysed

Mixing said reagent and water sample to form a solution

Measuring the absorbance of the resulting solution at 2 or more wavelengths

Determining from said absorbance measurements the concentration in solution of the reference compound [ref] and hence the concentration of reactant added as F×[ref].

If the concentration of reactant added is considered to be sufficient to provide an excess for the analyte concentration range of interest, determining the analyte concentration in solution from said measured absorbance Determining the volume V of reagent added from the reference concentration, the known concentration of reference in the reagent and the analysis chamber volume (CV)

Determining a new volume Vnew to be added to produce a chosen reactant excess

Regulating the dispensing system to dispense Vnew in the next analysis cycle

The reagents and method described herein are particularly well suited for use with the apparatus and method previously described in applicants earlier patent application WO2008061315, but may be used with other apparatus. For illustrative purposes only, free chlorine has been chosen as an example of an analysis but it will be understood the principles disclosed in the invention may be wholly or partially embodied in other analyses.

The invention also provides an optical method of analysis of total alkalinity using a single reagent and a volume control algorithm. The reagent and method utilises a pH indicator which is coloured in both acid and base forms.

A method for measurement of total alkalinity wherein the method comprises the steps of:

Adding an amount of a concentrated reagent to a water sample to be analysed, wherein the reagent contains a known concentration of acid and a known concentration of a pH indicator; and wherein the pH indicator is coloured in both acid and base forms and has a significant change in colour at pH values below that of the titration end point of the buffer present in the water sample; and wherein the concentration of acid is present in the reagent in a known concentration ratio to the pH indicator, such that the concentration of the acid may be expressed as some factor F multiplied by the concentration of the pH indicator.

Mixing said reagent and water sample to form a solution

Measuring the absorbance of the solution at 2 or more wavelengths

Determining from said absorbance measurements both the total concentration (acid+base forms) of indicator present in solution and the pH of the solution If the pH is within the colour change range of the pH indicator, determining the excess concentration of hydrogen ions present in the solution from the pH Determining the total concentration of acid added from the total concentration of the indicator.

Determining the total concentration of acid consumed in solution as the difference between the total concentration added and the excess remaining.

Determining the volume V of reagent added from the total indicator concentration, the known concentration of pH indicator in the reagent and the analysis chamber volume (CV)

Determining a new volume Vnew to be added to produce a chosen acid excess, i.e. a chosen pH within the colour change range of the pH indicator Regulating the dispensing system to dispense Vnew in a subsequent analysis cycle Another example of an analysis embodying the control system and aspects of the invention involves the use of a single reagent for analysing calcium hardness.

This invention provides a method for measurement of calcium hardness wherein the method comprises the steps of:

Adding an amount of a concentrated reagent to a water sample to be analysed, wherein the reagent contains a known concentration of a compound which binds strongly to calcium in a colourless form, and a known concentration of a compound which binds to calcium with two different colours in the bound and unbound forms but less strongly than the colourless strong binding compound; and wherein the concentration of colourless calcium binding compound is present in the reagent in a known concentration ratio to the coloured binding compound, such that the concentration of the colourless binding compound may be expressed as some factor F multiplied by the concentration of the coloured binding compound.

Mixing said reagent and water sample to form a solution

Measuring the absorbance of the solution at 2 or more wavelengths

Determining from said absorbance measurements both the total concentration of coloured binding compound and the proportions of the coloured calcium binding compound in bound and unbound forms present in the solution If there are significant proportions of both bound and unbound forms of the coloured binding compound present in the solution, determining the calcium hardness from concentrations of the bound coloured compound and the concentration of colourless binding compound Determining the volume V of reagent added from the total coloured binding compound concentration Determining a new volume Vnew to be added to produce a chosen coloured binding compound excess, i.e. a chosen ratio of bound to unbound forms Regulating the dispensing system to dispense Vnew in a subsequent analysis cycle The single reagent comprises a colourless compound which binds strongly to calcium (e.g. EDTA, sodium gluconate), a compound which binds less strongly to calcium and has a different colour in the bound and unbound form (e.g. Alizarin Red S), a pH buffer to maintain a narrow pH range, and may also contain a reducing agent such as sodium thiosulfate to remove any bleaching effect of oxidising agents on the coloured compound which may be present in the solution being analysed, and may also contain other compounds such as glycerol to alter the viscosity of the reagent solution.

EDTA and sodium gluconate are known to strongly complex calcium ions in solution, the resulting complex being colourless. Alizarin Red S is also known to complex calcium ions in solution, but not as strongly, so any calcium ions present will first be bound by the EDTA or sodium gluconate. The Alizarin Red S is red in colour in the unbound form and purple when bound to calcium when the pH is around 8.5. It is important to maintain the pH within a relatively small range, as Alizarin Red S also functions as a pH indicator and may be red or purple depending on the pH. As reagent is added the strong binder (EDTA or sodium gluconate) will bind first to any calcium present, and if the concentration of calcium is in excess of what can be bound by the strong binder then the Alizarin Red S will bind calcium and turn purple. If the calcium concentration is less than can be bound by the strong binder the Alizarin Red S will remain red.

The essence of this inventions methodology is converging on a volume of reagent to be added to give a required excess of a compound in the reagent at which point the parameter being analysed can be determined. Once in the volume range of interest this volume is then adjusted on the basis of concentrations measured to maintain this required excess and is the volume of reagent injected on the next analysis cycle. So when concentrations being analysed change slowly (which is often the case) the system usually only needs to make one injection to get a result and will track the required volume to be injected as that changes. This means a faster analysis time and less use of reagent than performing a titration each time. If there is a sudden large change then a few cycles are needed to converge back into the region of interest. The concentrations involved (and from that volumes injected) are calculated by using coloured reference compounds in the reagent which may or may not take part in the reaction.

The analysis examples described which fit this control method are:
1. Free chlorine using brilliant blue food dye. Here the method is tuning for a small excess of unreacted brilliant blue to make sure enough has been added to react with all the chlorine present. The unreacted brilliant blue and its oxidised product are used as the optical reference for how much reagent has been added.
2. Total alkalinity. Here the method is tuning for a small excess of acid beyond the end point to give a pH in the range measurable by bromophenol blue. Both acid and base forms of the bromophenol blue are used as the optical reference for how much reagent has been added.
3. pH. The method uses the ratio of the absorbance at 2 wavelengths to determine the pH, but the method uses the acid and base forms of the indicator as an optical reference to determine how much has been added (same as above with bromophenol blue) and then regulate to a fixed amount (excess) of reagent added.
4. Hardness. Here the method uses the bound and unbound forms of Alizarin Red S with calcium as an optical reference to determine how much reagent has been added, and then tuning to a fixed excess of unbound Alizarin Red S, so that it is in the range where some of the Alizarin is bound and some unbound.

DETAILED DESCRIPTION OF THE INVENTION

A preferred embodiment of the invention will be described with reference to the drawings in which.

In the case of the reagent bleaching to a colourless compound, incremental volumes may be added until an excess of reagent remains as indicated by the persistence of colour of the reagent. The amount of reagent remaining in excess can be calculated from the absorption of the reagent at one or more wavelengths. The total amount of reagent added can be calculated from the total volume of reagent added and the concentration of the reagent solution. The amount of reagent consumed will be the total added less the amount remaining in excess. The amount of free chlorine present can then be calculated from the amount of reagent consumed and the stoichiometry of the reaction between the reagent and free chlorine. Once the free chlorine concentration is known, the volume required to produce a given excess of reagent can be calculated and used in a control algorithm which uses this volume as the starting point for the next analysis and continually adjusts this starting volume up or down on the basis of each measurement to maintain this required excess regardless of the free chlorine concentration. This provides much more economical use of reagent, and a larger measurement range than simply adding a fixed volume of reagent sufficient to cover the concentration range of interest, and faster response than performing a stepwise titration each time. In many instances the free chlorine level will change relatively slowly and under this control strategy the volume of reagent added will track with the change in free chorine level. Significantly larger or smaller additions will only need to be performed to find the new required volume if there is a rapid change in the free chlorine level such as in a super chlorination event.

Figure 1:
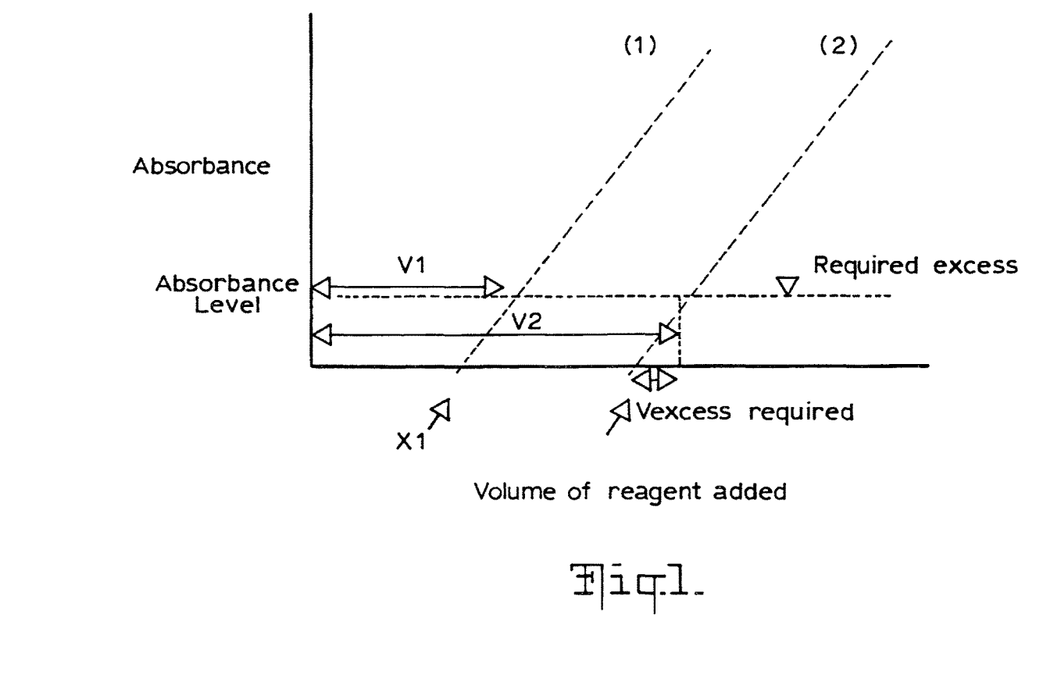
FIG. 1 shows the absorbance at a particular wavelength of the reagent dye as a function of volume added.

The principle of this control for the bleaching case is shown in FIG. 1, which shows the absorbance at a particular wavelength of the reagent dye as a function of volume added for two different free chlorine concentrations (1) and (2) where (2) represents a higher concentration. Initially at low volumes added all the reagent dye is bleached to a colourless product and there is no appreciable absorbance until sufficient dye has been added to react with all the free chlorine present, corresponding to the volumes indicated by X1 and X2. In the lower free chlorine case (1) excess dye is present at volumes greater then X1, and at volumes greater then X2 in the higher concentration case (2). As the excess increases so too does the measured absorbance of the reagent dye. To achieve the desired excess level indicated volumes V1 and V2 must be added in the low and high free chlorine cases respectively. The amount of reagent required in excess can be expressed as a volume (Vexcess_required). Once reagent dye is detected the excess amount (and corresponding excess volume Vexcess) can be calculated from the absorbance. The total volume V added can then be expressed as the sum of the volume of excess reagent and the volume which corresponds to the amount of reagent dye oxidised to the colourless product (Vproduct):

$$V = V\text{excess} + V\text{product}$$

Thus the new volume for the next cycle of analysis to regulate to the required reagent excess (e.g. V1 or V2 in FIG. 1) is:

$$V\text{new} = V\text{product} + V\text{excess\_required}$$

For each subsequent measurement this cycle is repeated: Vexcess is calculated from the absorbance of the reagent dye and knowing the total volume V added allows calculation of Vproduct and Vnew. The free chlorine concentration may be calculated from Vproduct which provides the amount of reagent dye which has reacted with the free chlorine.

An alternative to using an accurate mechanical volume dispensing means is a method for deriving the total amount of reagent added based on a reference compound added to the reagent as described in our corresponding patent number WO2008061315. The reference compound is a compound added to the reagent which does not take part in the reaction with the target analyte and has an absorption spectrum significantly different to other compounds present in the reagent and/or reaction products formed. The amount of reagent added can then be determined from the absorption (and hence concentration) of the reference compound. In this case the reference compound must not be appreciably oxidised by the free chorine or other oxidising compound being analysed.

Figure 2:
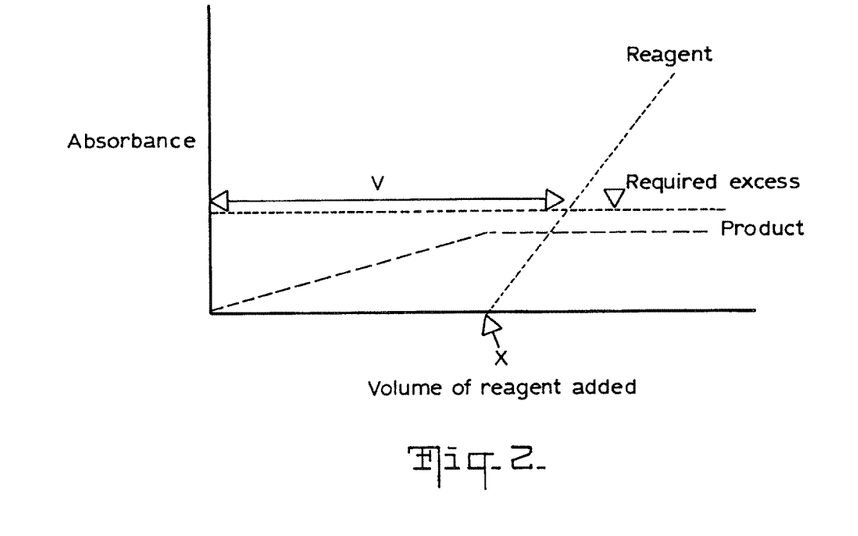
FIG. 2 shows the absorption profiles as a function of volume added for reagent dye and coloured product.

In the case of the reagent dye being oxidised to another colour, again incremental volumes of reagent can be added until an excess of the reagent persists (which will also be indicated by no further increase in the level of product produced). In this case the free chlorine concentration may be calculated either from the amount of reagent consumed as in the bleaching case, or the amount of product produced which can be determined from the absorption of the coloured product. FIG. 2 shows the absorption profiles as a function of volume added for reagent dye and coloured product, and the profiles will usually be measured at different wavelength for each of the reagent dye and oxidised product. The profile for the dye shows the same form as for the bleaching case except that since the product is not colourless there may also be a contribution to the absorbance measured from the product species and the absorbance at volume less than X may be non zero. The coloured product absorbance will tend to increase and then plateau off once all of the free chlorine has reacted, with any continued increase being due to a contribution to the absorbance from excess reagent dye. Given that there will in practice generally be some absorbance spectral overlap between reagent dye and product species the control algorithm needs to take this into account when deriving Vexcess and Vproduct.

For example if we consider two wavelengths where the absorption of the reagent dye and product species is appreciably different, such as a wavelength in the red and a wavelength in the blue in the case of Brilliant Blue and its oxidation product, then the relationships can be expressed as:

Red Absorbance (Rabs)=Red absorbance of excess reagent dye (Rexcess)+Red absorbance of product (Rproduct)

Blue Absorbance (Babs)=Blue absorbance of excess reagent dye (Bexcess)+Blue absorbance of product (Bproduct)

On the basis of the absorption spectrums for the pure compounds it is known what the relationship is between the absorbance at any wavelength. For example the blue absorbance of the reagent dye can be expressed as a factor $F1$ of the red absorbance, and the red absorbance of the product can be expressed as a factor $F2$ of the blue product absorbance. Therefore:

Rabs=Rexcess+$F2$×Bproduct

Babs=$F1$×Rexcess+Bproduct

Bproduct=(Babs−$F1$×Rabs)/(1−$F1$×$F2$)

Rexcess=Rabs−$F2$×Bproduct

Similarly relationships between other wavelengths can also be used.

The concentration of product (and hence concentration of free chlorine) is proportional to the blue absorbance of the product Bproduct, and the concentration of excess dye is proportional to the red absorbance of excess dye Rexcess.

Knowing the analysis chamber volume and the concentrations present in the reagent (or the absorbance for a given ratio of reagent to water), as described above for the bleaching case, the concentrations of both the excess reagent dye and product can be expressed as an equivalent volume of reagent added. So the volume added which is consumed to form product is Vproduct and the volume of reagent which if unreacted produces the absorbance Rexcess is Vexcess and hence as above the total volume V added is:

V=Vexcess+Vproduct, and again the new volume to add on the next measurement cycle to maintain the desired excess level is:

Vnew=Vproduct+Vexcess_required

As with the bleaching case a separate reference compound can be added to the reagent which has a significantly different absorption spectrum to compounds in the reagent and reaction products, and used to derive the amount of reagent added. However when a coloured reaction product is produced the resulting solution is used as its own reference to determine volumes of reagent added. The total amount of reagent added is derived from the relationship between the absorption spectrums of the reagent and product. The use of the solution as its own reference for deriving the amount of reagent negates the need for an additional reference which is stable to free chlorine oxidation. If the absorption at a particular wavelength saturates the absorption relationships at other wavelengths can be used. Determination of the volumes added via optical means allows the use of volume injection methods other than those involving accurate mechanical mechanisms, for example a time based pressurised injection system as per our corresponding patent WO2008061315. Deriving the volume added optically also serves as a useful diagnostic.

It can be seen that the reagent and control method of the invention for free chlorine analysis has several advantages. In a preferred embodiment the reagent simply involves a solution of Brilliant Blue FCF together with a means of buffering the reagent to the preferred pH range of 1.5-2.5. The buffering may be accomplished by using combinations of organic and/or inorganic acids, bases and their salts. In a preferred embodiment the buffering means is citric acid or tartaric acid in conjunction with amino acids such as glycine and/or aspartic acid. In another preferred embodiment the buffering means is a phosphate buffer comprising phosphoric acid and sodium dihydrogen phosphate. The former compositions have the advantage they are not corrosive, non-toxic and do not promote algae growth in the case where the reagent is returned to a swimming pool. The control method is based on deriving volumes from optical measurements of the unreacted reagent dye and coloured oxidation product at two or more wavelengths and using these volumes to calculate a new volume to be injected in the next measurement cycle in order to maintain a chosen excess of unreated reagent dye. The control method provides economical use of reagent and extends the concentration range which can be measured.

In accordance with the objects of the invention, it can be seen that the use of a food dye overcomes the toxicity concerns of DPD and methyl orange, allowing the reaction mixture to be fed back into the supply water in order to minimise water consumption.

Moreover, it has been found in practice that regulation of the volume of food dye reagent added to the water sample according to nominated absorbance values of the parent food dye, reaction product and reference compound if present, or combinations thereof, allows accurate measurements of free chlorine over the range 0-25 ppm.

It was also noted that a slow reaction of Brilliant Blue FCF occurs with chloramines. It is another aspect of the invention to use the kinetics of this reaction to determine combined chlorine content of the fluid sample. Any free chlorine present will effectively react instantly with the Brilliant Blue FCF and the reaction with chloramines (and some other oxidising agents) will proceed much more slowly. In this case the evolution of reaction product over time can be used to determine concentrations present. Either the reaction can be monitored for a long time until the reaction has completed and the absorption level of the product plateaus, or the reaction (absorbance level of the product) may be monitored as a function of time and a mathematical function fitted to the data with the final concentration of product being calculated from the fitted function.

Examples of reagent formulations are:

A
232 gm Phosphoric Acid 85% w/w
293 gm Sodium Dihydrogen Phosphate Dihydrate
1.8 gm Brilliant Blue (Erioglaucine) Food Dye C133
Made up to 1 L with distilled water B
232 gm Phosphoric Acid 85% w/w
293 gm Sodium Dihydrogen Phosphate Dihydrate
1.8 gm Brilliant Blue (Erioglaucine) Food Dye C133
0-300 g glycerol
Made up to 1 L with distilled water C
150 gm glycine
700 gm citric acid
1.8 gm Brilliant Blue (Erioglaucine) Food Dye C133
Made up to 1 L with distilled water D
150 gm glycine
500 gm tartaric acid
100 gm aspartic acid
1.8 gm Brilliant Blue (Erioglaucine) Food Dye C133
0-300 gm glycerol
Made up to 1 L with distilled water Other buffers may be used—the object is to produce a resultant pH in the range 1.5-2.5 after addition of the reagent in the ratio 1:100 (reagent:water sample being analysed). Other concentrations of Brilliant Blue may also be used depending on the requirements of the absorption electronics.

In another aspect of this invention a combination of food dyes are utilised in a manual test kit for free chlorine or other oxidising compounds. If two or more food dyes, which may be bleached or transformed to a coloured product in proportion to the amount of free chlorine present, are included in a reagent for free chlorine it will be possible to generate a range of colours in the resulting solution such that a colour scale proportional to the free chlorine may be created which is distinguishable by eye.

Whenever the reagent compound(s) is coloured and the reaction product(s) are coloured the resulting solution can be used as its own reference to derive the volume of reagent added as described above. Another particular case of this is pH indicators where the acid and base forms are both coloured. In this case the resulting solution consists of a mixture of the acid and base forms of the indicator, the ratio of which depends on the pH. As above the concentrations of both species can be derived from the absorbance relationships at two or more wavelengths. The total concentration of indicator will be the sum of the two forms, and the total concentration can be converted to an equivalent volume added.

For example the pH of a swimming pool is conveniently measured using phenol red as the indicator dye. Phenol red changes from yellow to red over the pH range 6.8 to 8.4, The pH can be determined optically using a single reagent consisting of a pH indicator dye and, in the case of swimming pool water, an additional reducing agent (such as sodium thiosulfate) to neutralise the free chlorine to prevent bleaching of the indicator. The total concentration and volume added during any measurement can be derived from the absorption at two or more wavelengths. The pH can be calculated from a single wavelength absorbance once the total amount of indicator added is known, or the pH can be calculated from the ratio of absorbance at two or more wavelengths.

Figure 3:
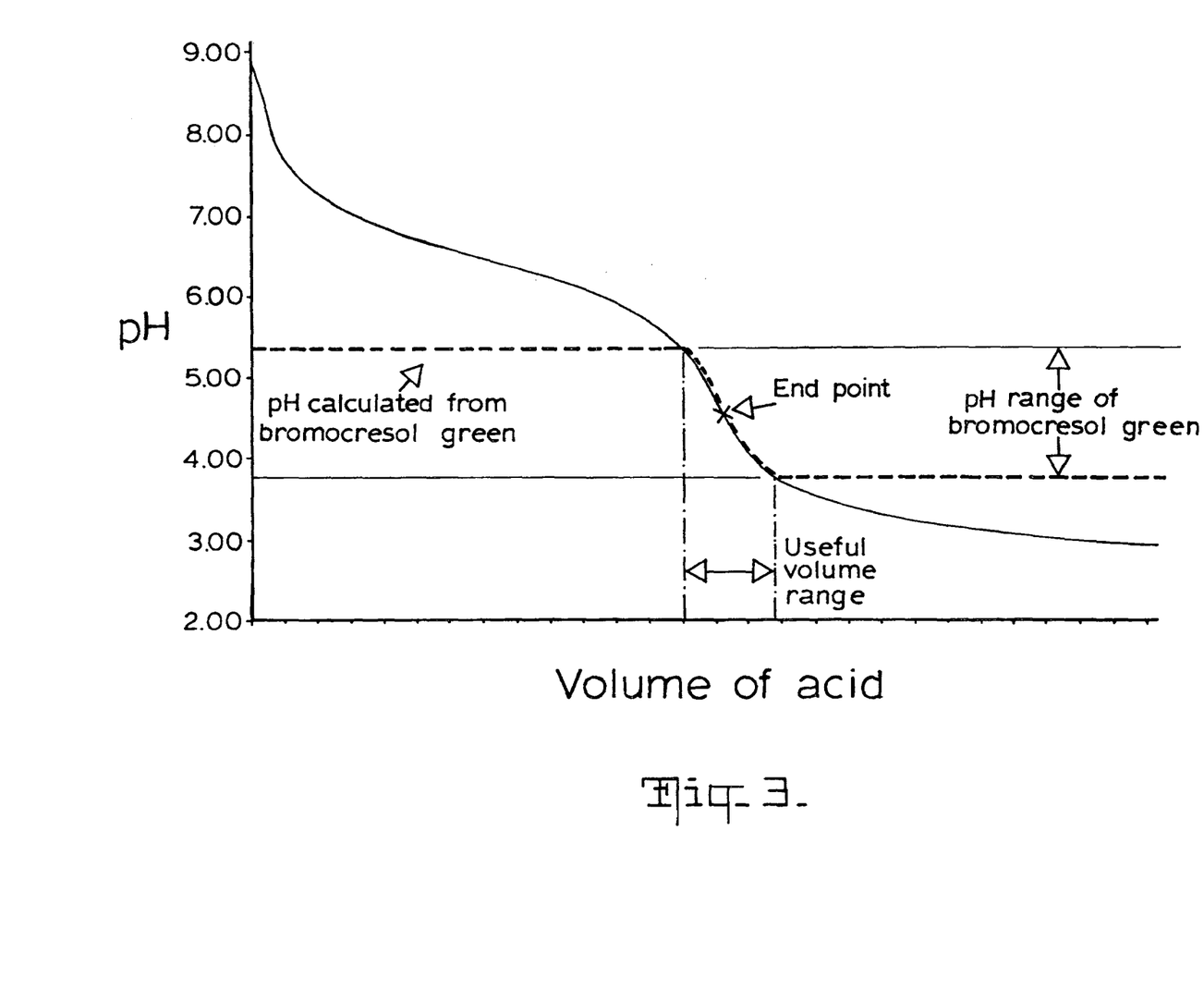
FIG. 3 illustrates the control system applied to a the titration to determine total Alkalinity.

In another aspect this invention provides an optical method of analysis of total alkalinity using a single reagent and a volume control algorithm. The reagent and method utilises a pH indicator which is coloured in both acid and base forms. The pH indicator functions as its own reference for deriving the total volume added. In many applications the total alkalinity is regulated using sodium bicarbonate. Typically total alkalinity (TA) is determined via a titration with acid to locate the carbonic acid end point. The TA is calculated from the amount of acid added at the end point. As acid is progressively added to the solution being analysed the pH decreases, and changes most rapidly in the vicinity of the end point, as shown in FIG. 3.

A pH indicator only allows the pH to be calculated accurately within the pH range where it changes colour. Outside this range the indicator will be predominantly in the acid or base form and effectively remain the same colour as the pH is varied. For an indicator which changes colour in the pH region of the end point (for example bromocresol green) the pH calculated using the colour of the indicator during the titration appears as the dashed line shown in FIG. 3. In order to determine the end point acid must be added until the pH passes through the region of colour change of the indicator. Acid could be added continuously provided adequate and fast mixing occurs during the addition, or in a stepwise fashion. At each point it is necessary to know the volume of acid reagent added to determine the volume added at the end point represented by the point of inflection on the titration curve. If the indicator is added to the reagent the concentration of indicator present increases in proportion to the amount of reagent added. Indicators with coloured acid and base forms can be used as their own reference for calculating the amount of indicator present and hence the volume of reagent added. Once the TA is known the volume of reagent necessary to reach the pH region near the end point can be calculated and used as the starting point for the next analysis cycle. Performing this calculation at each analysis cycle will allow the control routine to quickly zero in on the region of interest and track with changes in the TA.

In another aspect this invention provides a single reagent for analysis of total alkalinity consisting of an acid, a pH indicator which has both a coloured acid and base form, and where free chlorine or other oxidising agent is present in the water to be analysed, a reducing agent to neutralise the oxidising agent to prevent bleaching of the pH indicator dye. All compounds need to coexist stably in the one solution. In a preferred embodiment the reducing agent is colourless and is oxidised to a colourless product. The single reagent may also contain other compounds for other purposes such as altering the viscosity of the reagent.

Figure 4:
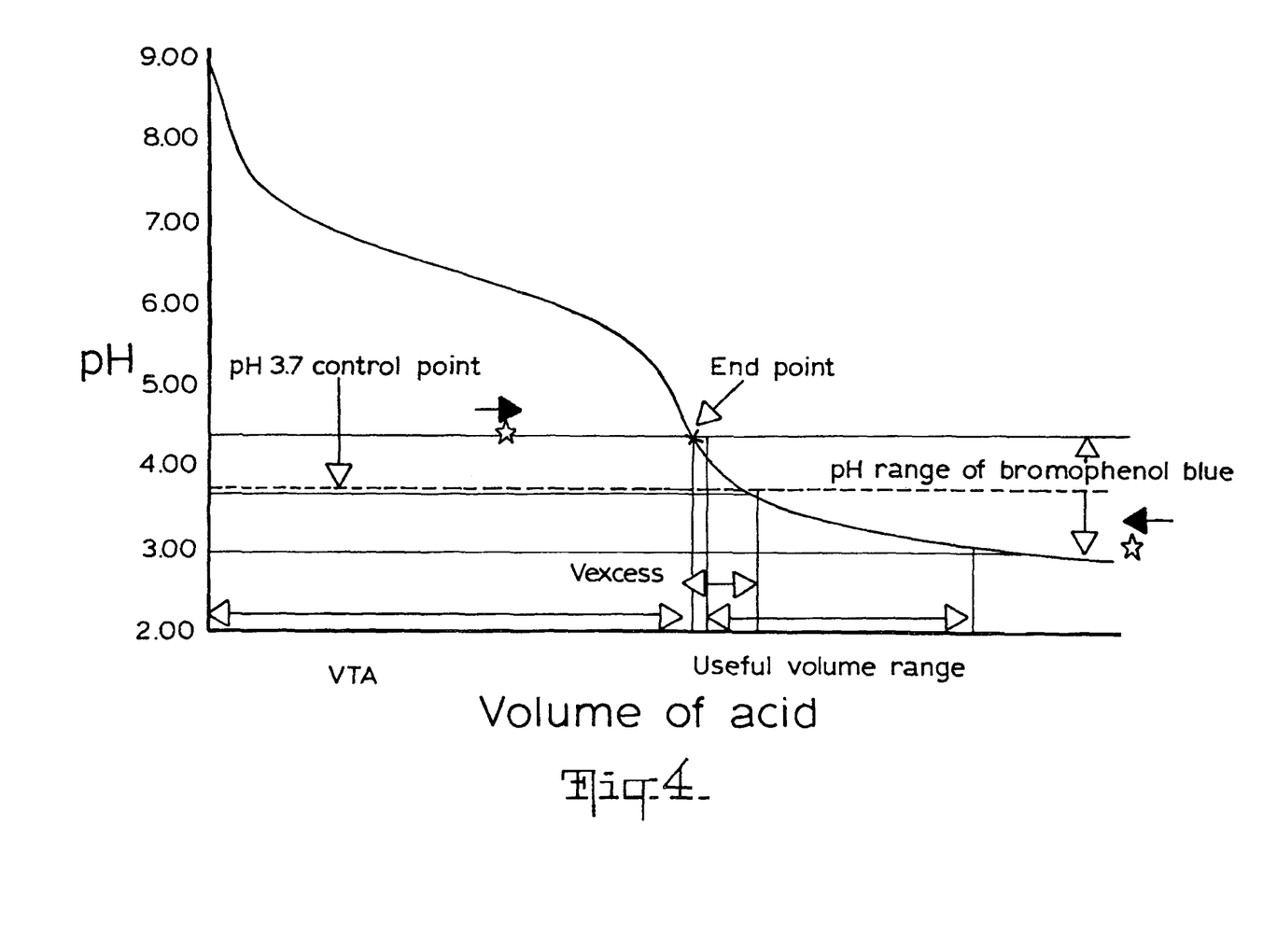
FIG. 4 illustrates a second method of measuring total alkalinity.

The preferred embodiment of the invention is not to perform a titration to determine TA, but rather a single volume addition of the single TA reagent to add an excess of acid beyond the end point and calculate the TA from the excess of acid present. The advantage of this approach is only a single point past the end point is required and it is not necessary to determine the point of inflection in the titration curve. Also since an excess of acid is required a concentrated reagent can be used and only small volumes are required to be added, minimising reagent usage and minimising any dilution effects from adding the reagent. In this method a pH indicator (for example bromophenol blue) is chosen which changes colour at pH values below the end point as shown in FIG. 4. The rate of change of the pH versus volume of reagent added curve is also much lower beyond the end point so a much wider range in volume of reagent can be added to produce a pH which falls within the range which can be measured by the indicator (indicated by "useful volume range" in FIGS. 3 and 4). The volume added can be calculated using the bromophenol blue as its own reference, and the pH is also calculated using the absorbance values of the indicator.

The total amount of acid added is calculated from the total amount of reagent added. In the TA analysis the excess required is an excess of acid beyond that to completely convert all the bicarbonate to carbonic acid, analogous to the free chlorine analysis where the excess required was unreacted reagent dye beyond that required to react with all the free chlorine. In this instance the concentration of excess of acid can be calculated directly from the pH. The TA is calculated from the amount of acid consumed. The concentration of acid consumed is the difference between the total concentration added and the concentration remaining in excess. The amount of acid consumed can be expressed as a volume added, which is the volume of reagent added when at the end point (VTA).

Bromophenol blue changes from yellow to blue over the pH range 3 to 4.4. The control algorithm of the preferred embodiment regulates the volume added to achieve a pH in the middle of this range, i.e. pH 3.7. The amount of reagent required to produce a pH of 3.7, which is a particular excess of acid beyond the end point (i.e. in an un-buffered solution) can be expressed as a volume of reagent (Vexcess). Thus the new volume of reagent to add to achieve a pH of 3.7 is:

$$V_{new} = V_{TA} + V_{excess}$$

Again this value is re-calculated after each analysis cycle and the algorithm will track with changes in TA. It will only be necessary to make more significant changes to the volume injected if there is an event which rapidly changes the TA by a large amount. In this case the volume added will be increased or decreased to re-locate the region of colour change of the bromophenol blue. The direction of change (increase or decrease in added volume) is evident from the calculated pH value. As discussed above the pH calculated using the indicator when the pH is outside the range of colour change of the indicator, will be a relatively constant value since the indicator will be present as primarily all base form or all acid form. Thus if the pH calculated from the indicator is close to or higher than 4.4 more reagent needs to be added, and if the pH calculated is close to 3 or lower, then less reagent needs to be added (as illustrated by the positions in FIG. 4 marked by stars).

Example reagent formulations for Total Alkalinity
E
10-30% water
0-40% glycerol
0.02-0.5 molar final HCl concentration (typically 0.1M)
0.1-5 g/liter thiourea
1-4 g/L bromophenol blue
Balance ethanol
F.
10-30% water
0-40% glycerol
0.02-0.5 molar final HCl concentration (typically 0.1M)
0.1-5 g/liter glucathione
1-4 g/L bromophenol blue
Balance ethanol
G
10-30% water
0-40% glycerol
0.02-0.5 molar final HCl concentration (typically 0.1M)
0.1-5 g/liter cysteine
1-5 g/L bromophenol blue
Balance ethanol HCl (hydrochloric acid) can be substituted by other strong acids such as sulphuric ($H_2SO_4$) or sodium hydrogen sulphate ($NaHSO_4$).

A reagent formulation for pH
H
0.05-0.5 g/liter Phenol Red (or other indicator for appropriate pH range)
0-50% ethanol
0-50% glycerol
0.1-5 g/liter sodium thiosulfate
Balance water Another embodiment of the control strategy of the invention involves the use of a single reagent for analysing calcium hardness.

The method involves determining the volume of reagent to add such that the concentration of strong binder plus Alizarin Red S is slightly in excess of what is required to bind all of the calcium present. The volume added will be adjusted to attain the point where half of the Alizarin Red S is bound to calcium (purple form) and half is unbound (red form). The method is thus analogous to the method described for total alkalinity where the amount of Alizarin Red S in excess unbound form and the total amount of reagent added, is determined from the Alizarin Red S absorption at two or more wavelengths (cf pH indicator). Once a volume of reagent has been added which results in a mixture of bound and unbound forms of the Alizarin Red S being present, the calcium hardness can be calculated from the proportion of bound Alizarin Red S (calculated from the ratio of the two colour forms) and the total amount of Alizarin Red S added (calculated from the absorption magnitudes at two or more wavelengths). Since the Alizarin Red S and the strong binder are present is a fixed ratio in the reagent the total amount of Alizarin Red S added is related to the amount of strong binder added. The calcium concentration will then be related to the concentration of strong binder plus the concentration of bound Alizarin Red S.

To converge on the volume range required the direction of whether to add more or less reagent is indicated by the absorption of the Alizarin Red S in the solution. If the Alizarin Red S is all in the red form more reagent needs to be added as it is all in unbound form, and if it is all in the purple form less reagent needs to be added as it is all in the bound form. Once the required volume range has been determined this volume is then used in the next analysis cycle so it will track with slow changes in hardness.

Preferred reagent formulations for calcium hardness
I
10-200 g/liter TRIS 3.5-70 ml/liter conc. HCl (e.g. 40 g/L TRIS, 14 ml/L conc. HCl)
0.5-5 g/liter Alizarin Red S
1-15 g/liter EDTA
0-50% glycerol
J.
10-200 g/liter TRIS
3.5-70 ml/liter conc. HCl
0.5-5 g/liter Alizarin Red S
1-50 g/liter sodium gluconate
0-50% glycerol From the above it can be seen that this invention provides a unique and safe approach to measuring chlorine, pH, total alkalinity and calcium hardness. Those skilled in the art will realise that this invention may be implemented in embodiments other than those described without departing from the core teachings of the invention.

The invention claimed is:

1. A colorimetric analytical method for determining the concentration of an oxidising analyte present in a liquid sample that contains the oxidising analyte which method comprises:
   a) mixing a volume of reagent with a volume of said liquid sample to form a solution,
   b) wherein said reagent contains a single food dye capable of reacting with said oxidising analyte so that the reaction product in the said solution has different absorbance wavelength characteristics from the un-reacted food dye;
   c) measuring the absorbance characteristics of said solution at two or more wavelengths, wherein at least one of the wavelengths corresponds to the un-reacted food dye and at least one other of the wavelengths corresponds to reacted food dye;
   d) determining the concentration of said reaction product of said food dye and concentration of un-reacted food dye in said solution from said absorbance measurements; and
   e) determining the concentration of said oxidising analyte from the concentration of said reaction product and said concentration of un-reacted food dye.

2. The method as claimed in claim 1 wherein the oxidizing analyte is chlorine.

3. The method as claimed in claim 1 wherein the adding a volume of reagent, mixing, measuring absorbance and determining concentrations of said reaction product of said food dye and said un-reacted food dye are repeated until there is a non-zero concentration of un-reacted food dye to indicate an excess of reagent has been added beyond that required for stoichiometric reaction between said food dye and said oxidising analyte and determining the concentration of said oxidising analyte from the concentration of said reaction product and said non-zero concentration of un-reacted food dye.

4. The method as claimed in claim 1 wherein the reagent also includes a compound or compounds for restricting the pH of said solutions to a desired value or range.

5. The method as claimed in claim 2 wherein the reagent also includes a compound or compounds for restricting the pH of said solutions to a desired value or range.

6. The method as claimed in claim 3 wherein the reagent also includes a compound or compounds for restricting the pH of said solutions to a desired value or range.

7. The method as claimed in claim 1 wherein said single food dye is Brilliant Blue FCF.

8. The method as claimed in claim 4 wherein said compound or compounds for restricting pH comprises tartaric acid or a phosphate buffer.

9. The method as claimed in claim 1 wherein a coloured reference compound which does not react with said oxidising compound in said liquid sample is included in the reagent.

10. The method as claimed in claim 1 wherein the volume of reagent determined to produce a preselected excess concentration of un-reacted food dye in said solution is used as the starting volume of reagent added in the next analysis of said oxidising compound concentration.

11. The method as claimed in claim 1 wherein for reactions which are not instantaneous the reaction is monitored as a function of time to determine the concentration of said oxidising analyte.

12. The method as claimed in claim 5 wherein said compound or compounds for restricting pH comprises tartaric acid or a phosphate buffer.

13. The method as claimed in claim 6 wherein said compound or compounds for restricting pH comprises tartaric acid or a phosphate buffer.

14. The method as claimed in claim 4 wherein a coloured reference compound which does not react with said oxidising compound in said liquid sample is included in the reagent.

15. The method as claimed in claim 3 wherein a coloured reference compound which does not react with said oxidising compound in said liquid sample is included in the reagent.

16. The method as claimed in claim 4 wherein a coloured reference compound which does not react with said oxidising compound in said liquid sample is included in the reagent.

17. The method as claimed in claim 5 wherein a coloured reference compound which does not react with said oxidising compound in said liquid sample is included in the reagent.

18. The method as claimed in claim 6 wherein a coloured reference compound which does not react with said oxidising compound in said liquid sample is included in the reagent.

* * * * *